United States Patent
Jeong et al.

(10) Patent No.: US 7,580,028 B2
(45) Date of Patent: **\*Aug. 25, 2009**

(54) APPARATUS AND METHOD FOR SELECTING AND OUTPUTTING CHARACTER BY TEETH-CLENCHING

(75) Inventors: Hyuk Jeong, Daejeon (KR); Jong Sung Kim, Daejeon (KR); Wookho Son, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 610 days.

This patent is subject to a terminal disclaimer.

(21) Appl. No.: 11/407,431

(22) Filed: Apr. 20, 2006

(65) Prior Publication Data

US 2007/0164985 A1    Jul. 19, 2007

(30) Foreign Application Priority Data

Dec. 2, 2005    (KR) .................. 10-2005-0116806

(51) Int. Cl.
*G09G 5/00*    (2006.01)
(52) U.S. Cl. ...................... 345/156; 345/157; 705/15
(58) Field of Classification Search ............... 345/156, 345/157; 341/21; 340/407.1; 600/545, 546, 600/590; 706/15

See application file for complete search history.

(56) References Cited

U.S. PATENT DOCUMENTS

| | | | | |
|---|---|---|---|---|
| 4,408,192 | A * | 10/1983 | Ward et al. | 340/407.1 |
| 5,474,082 | A * | 12/1995 | Junker | 600/545 |
| 6,222,524 | B1 * | 4/2001 | Salem et al. | 345/157 |
| 6,580,414 | B1 * | 6/2003 | Wergen et al. | 345/156 |
| 6,613,001 | B1 * | 9/2003 | Dworkin | 600/590 |
| 7,071,844 | B1 * | 7/2006 | Moise | 341/21 |
| 2003/0046254 | A1 * | 3/2003 | Ryu et al. | 706/15 |
| 2006/0061544 | A1 * | 3/2006 | Min et al. | 345/156 |
| 2006/0184059 | A1 * | 8/2006 | Jadidi | 600/546 |

FOREIGN PATENT DOCUMENTS

KR    10-2002 0092880    12/2002
KR    10-2004 0079150    9/2004

* cited by examiner

*Primary Examiner*—Amare Mengistu
*Assistant Examiner*—Premal Patel
(74) *Attorney, Agent, or Firm*—Ladas & Parry LLP

(57) ABSTRACT

An apparatus and method for selecting and outputting characters by making a teeth clenching motion for disabled person are disclosed. The apparatus includes: an electromyogram signal obtaining unit including electromyogram sensors disposed at both sides for generating an electromyogram signal according to a predetermined muscle activated when a disabled person clenches teeth, and a ground electrode connected to a body of the disabled persons for providing a reference voltage; and an electromyogram signal processing unit for outputting a character by identifying a teeth clenching motion pattern of each block according to a side of teeth clenched, a duration of clenching teeth and consecutive clenching motions through analyzing the obtained electromyogram and selecting characters according to the identified teeth clenching motion pattern.

12 Claims, 6 Drawing Sheets

FIG. 4a

| 1 space | 2 ABC | 3 DEF |
|---|---|---|
| 4 CHI | 5 GKL | 6 MNO |
| 7 PQRS | 8 TUV | 9 WXYZ |
| * | 0 | # |

FIG. 4b

| 1 EWQ | 2 TFY | 3 OP |
|---|---|---|
| 4 ADZ | 5 RGV | 6 ILJ |
| 7 SCX | 8 HUB | 9 NMK |
| * | 0 space | # |

FIG. 4c

| 1 ㄱㅁㅠ | 2 ㅅㅈㅋ | 3 ㅓㅕ |
|---|---|---|
| 4 ㄴㄷㄸ | 5 ㅇㅎㅌ | 6 ㅣㅜㅠ |
| 7 ㄹㅂㅃ | 8 ㅗㅆㅍ | 9 ㅏㅛㅑ |
| * | 0 ㅡㅊㅉ | # |

| 1(K1) CLS->CLL | 2(K2) CRL | 3(K3) CRS->CRL |
|---|---|---|
| 4(K4) CLS | 5(K5) SELECTED AS INITIAL KEY | 6(K6) CRS |
| 7(K7) CLS->CLS | 8(K8) CLL | 9(K9) CRS->CRS |
| *(K*) CLS->CLS->CLS | 0(K0) CLL->CLS(or CLL) | #(K#) CRS->CRS->CRS |

APPARATUS AND METHOD FOR SELECTING AND OUTPUTTING CHARACTER BY TEETH-CLENCHING

BACKGROUND OF THE INVENTION

1. Field of the Invention

The present invention relates to an apparatus and method for selecting and outputting a character by clenching teeth, and more particularly, to an apparatus and method for selecting and outputting characters based on electromyogram generated from a temporalis muscle when a quadriplegic disabled person clenches teeth.

2. Description of the Related Art

Disabled persons have various types of impairments. Generally, a person suffered by spinal cord damage is a quadriplegia which means a person paralyzes all four limbs.

Conventionally, a quadriplegic disabled person uses a voice recognition technology to input characters in an information terminal such as a mobile phone or a computer. Also, the quadriplegic disabled person uses a long stick by biting it with his teeth and touches a target key of a keyboard to input the characters into the information terminal. Furthermore, a motion sensor is used to detect the movement of disabled person's head to input characters. In this conventional method, a mouse is controlled based on the sensed head movement, and target keys displayed on a computer monitor are selected through controlling the mouse to input the selected characters into the computer.

However, such conventional methods of inputting characters in the information terminal have following problems. The voice recognition cannot be used when a user cannot talk or when there are serious noise. Also, the method of using the long stick makes a user tired and uncomfortable because the user must bit the long stick all the time while inputting the text. Therefore, such conventional methods give greater stresses on a user's neck and jaw. The conventional method of using the sensor also makes the user tired because the mouse is generally too sensitive to control through moving the head, and it requires such a deep concentration to control them.

SUMMARY OF THE INVENTION

Accordingly, the present invention is directed to an apparatus and method for selecting and outputting a character by teeth clenching, which substantially obviates one or more problems due to limitations and disadvantages of the related art.

It is an object of the present invention to provide an apparatus for selecting and outputting a character by clenching teeth, which is designed as a headgear such as a hat or a hair-band, by sensing and analyzing electromyogram signal generated by a teeth clenching motion of the disabled person, identifying the teeth clenching motion of the disabled person as a left teeth clenching motion, a right teeth clenching motion, a both teeth clenching motion and selecting and outputting a character according to the identified teeth clenching motion and a duration time for clenching the teeth so as to allow the disabled person to input character with minimized discomfort.

It is another object of the present invention to provide a method of selecting and outputting characters by making a teeth clenching motion including a) sensing an electromyogram signal of a predetermined muscle activated by a teeth clenching motion made by a user through electromyogram sensors; b) dividing the sensed electromyogram signal by a predetermined time, extracting characteristics from the divided electromyogram time blocks, comparing the extracted characteristic value with a predetermined threshold, classifying the divided electromyogram time block into an On-state if the extracted characteristic value are larger than the threshold, classifying the divided electromyogram time block into an Off-state if the extracted characteristic value is smaller than the threshold, identifying a basic teeth clenching motion pattern having one of values 'rest', 'left', 'right' and 'both' at a basic pattern identifying unit, selecting a key location allocated on a keyboard based on the identified basic teeth clenching pattern of each block, and selecting one of characters in the selected key through a teeth clenching motion to completely input a corresponding character at a command generating unit; and c) outputting the selected character on a character displaying unit.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, there is provided an apparatus for selecting and outputting characters by a teeth clenching motion made by a user, including: an electromyogram signal obtaining unit including electromyogram sensors disposed at both sides for generating an electromyogram signal according to a predetermined muscle activated when a disabled person clenches teeth, and a ground electrode connected to a body of the disabled persons for providing a reference voltage; and an electromyogram signal processing unit for outputting a character by identifying a teeth clenching motion pattern of each block according to a side of teeth clenched, a duration of clenching teeth and consecutive clenching motions through analyzing the obtained electromyogram and selecting characters according to the identified teeth clenching motion pattern.

In another aspect of the present invention, there is provided a method of selecting and outputting characters by a teeth clenching motion, including the steps of: a) sensing an electromyogram signal of a predetermined muscle activated by a teeth clenching motion made by a user through electromyogram sensors; b) dividing the sensed electromyogram signal by a predetermined time, extracting characteristics from the divided electromyogram time blocks, comparing the extracted characteristic value with a predetermined threshold, classifying the divided electromyogram time block into an On-state if the extracted characteristic value are larger than the threshold, classifying the divided electromyogram time block into an Off-state if the extracted characteristic value is smaller than the threshold, identifying a basic teeth clenching motion pattern having one of values 'rest', 'left', 'right' and 'both' at a basic pattern identifying unit, selecting a key location allocated on a keyboard based on the identified basic teeth clenching pattern of each block, and selecting one of characters in the selected key through a teeth clenching motion to completely input a corresponding character at a command generating unit; and c) outputting the selected character on a character displaying unit.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention, are incorporated in and constitute a part of this application, illustrate embodiments of the invention and together with the description serve to explain the principle of the invention. In the drawings:

FIGS. 4A through 4C show keypads having a 4×3 matrix type arrangement;

DETAILED DESCRIPTION OF THE INVENTION

Reference will now be made in detail to the preferred embodiments of the present invention, examples of which are illustrated in the accompanying drawings.

A character selecting and outputting apparatus according to the present invention selecting a target character and outputting the selected character by making a teeth clenching motion. The teeth clenching motion can be made by a disabled person having serious impairment by distinguishing a right teeth clenching motion, a left teeth clenching motion and a both side teeth clenching motion. A muscle used for clenching teeth is a masseter muscle around a jaw and a temporalis muscle at a temple. Since the masseter muscle is located at both side of jaw, it is not easy to attaché sensors around the masseter muscle. Although the sensor is attached at the masseter muscle, a user may be uncomfortable. In the present invention, the sensors are attached around temples of side head to obtain an electromyogram signal from the temporalis muscle. Since the sensors are disposed at a headgear such as a hair band or a hat, it minimizes discomfort of user and maximizes convenience.

Figure 1:
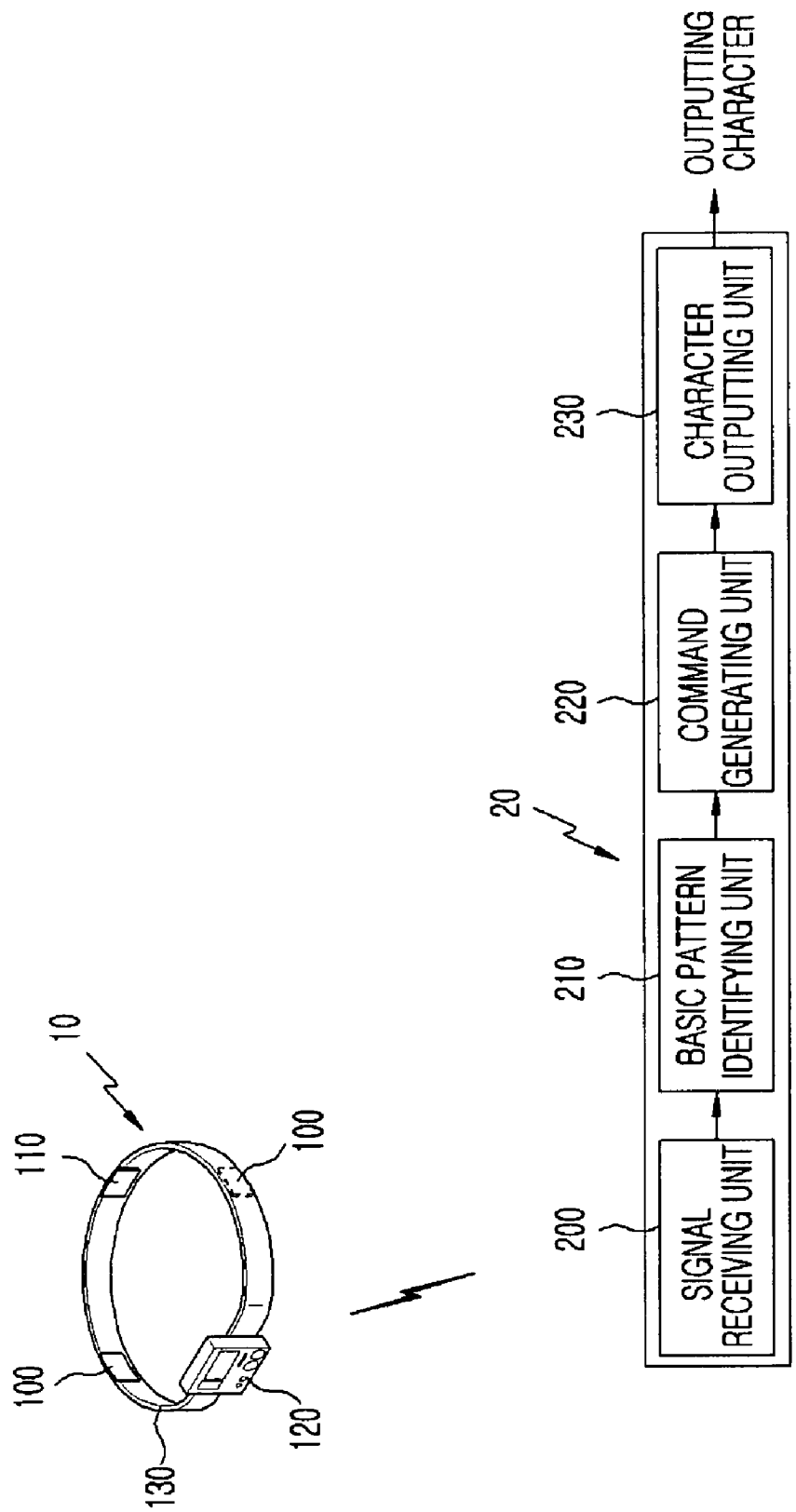
FIG. 1 is a conceptual view illustrating an apparatus for selecting and outputting a character by clenching teeth according to an embodiment of the present invention.

FIG. 1 is a conceptual view illustrating an apparatus for selecting and outputting a character by clenching teeth according to an embodiment of the present invention.

As shown in FIG. 1, the apparatus for selecting and outputting a character by clenching teeth according to the present embodiment includes a signal obtaining and transmitting unit 10 for obtaining an electromyogram signal and a signal processing unit 20 for processing the obtained electromyogram signals.

The signal obtaining and transmitting unit 10 includes two electromyogram sensors 100 for sensing electromyogram signals generated from a temporalis muscle when a teeth clenching motion made by a disabled person; a ground electrode 110 for measuring a reference voltage; and an amplifying and transmitting unit 120 for amplifying the sensed signal, transforming the amplified signal to a digital signal and transmitting the digital signal in wireless link.

The electromyogram sensors 100, the ground electrode 110 and the amplifying and transmitting unit 120 are disposed in a hair-band 130. It is preferable to design the hair-band 130 to be easily wearable according to ability of the disabled person. For example, Velcro is attached at an inside surface of the hair-band 130 to easily adjust a position of the electromyogram sensors 100 corresponding to conditions of a disabled person such as a shape of a head in order to accurately sense the electromyogram signal. In the present embodiment, the signal obtaining and transmitting unit 10 is disposed in the hair-band 130. However, the signal obtaining and transmitting unit 10 may be disposed in various types of headgears such as a hat or a cap 140.

The electromyogram sensor 100 uses voltage difference between two pairs of electrodes to obtain the electromyogram generated by the teeth clenching motion of the disabled person so as to secure a safety against an eye blanking motion and to minimize influence of electroencephalogram transferred from a brain. In the present embodiment, two sensors 100 are included. However, the present invention is not limited by the number of the electromyogram sensors.

The signal processing unit 20 includes a signal receiving unit 200, a basic pattern identifying unit 210, a command generating unit 220 and a character outputting unit 230.

The signal receiving unit 200 receives signal transmitted from the amplifying and transmitting unit 120 and outputs a digital signal.

The basic pattern identifying unit 210 divides the digital signal inputted from the signal receiving unit 210 into time blocks and identifies a basic teeth clenching pattern per each time block, such as pause, left side, right side and both sides.

The command generating unit 220 identifies a second pattern from the basic patterns of each block and selects or inputs characters according to the second pattern.

The character outputting unit 230 may be a display for displaying numbers, English alphabets, or Korean alphabets inputted from the user through teeth clenching motion and related information thereof. That is, the user inputs characters while watching a keyboard displayed on the character outputting unit 230.

In the present embodiment, the signal obtaining and transmitting unit 10 and the signal processing unit 20 communicate one another through a wireless link. However, they may be connected through a wired link. Also, the signal receiving unit 200, the basic pattern recognition unit 210 and the command generating unit 220 may be included into the signal obtaining and transmitting unit 10, for example, the signal amplifying and transmitting unit 120. And, the character outputting unit 230 may be only separately provided. In this case, a wired/wireless transmitting/receiving unit or an interface may be further included in both of equipments.

Figure 2:
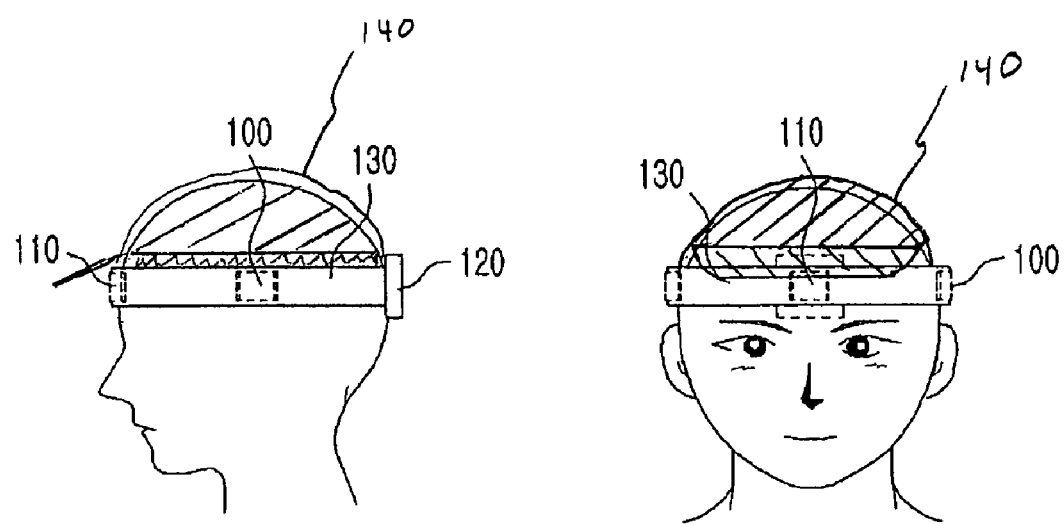
FIG. 2 is a view showing a disabled person wearing the apparatus for selecting and outputting a character by clenching teeth shown in FIG. 1.

FIG. 2 is a view showing a disabled person wearing the apparatus for selecting and outputting a character by clenching teeth shown in FIG. 1.

Referring to FIG. 2, the electromyogram sensors 100 and the ground electrode 110 are disposes inside of the hair-band 30 in parallel at proper positions so that the ground electrode 110 is arranged at a center of a forehead of a disabled person and the electromyogram sensors 100 are arranged at both side heads of the disabled person when the disabled person wears the hair-band 30. Since the electromyogram signal generated by the teeth clenching motion is easily detected around temples that are about 10 cm apart from an end of eyebrow formed on the temporalis muscle, the disabled person adjusts the hair-band to arrange the electromyogram sensors 100 around the temples after wearing the hair-band 30.

Hereinafter, a method of selecting and outputting a character by teeth clenching according to the present invention will be described with reference to accompanying drawings.

Figure 3:
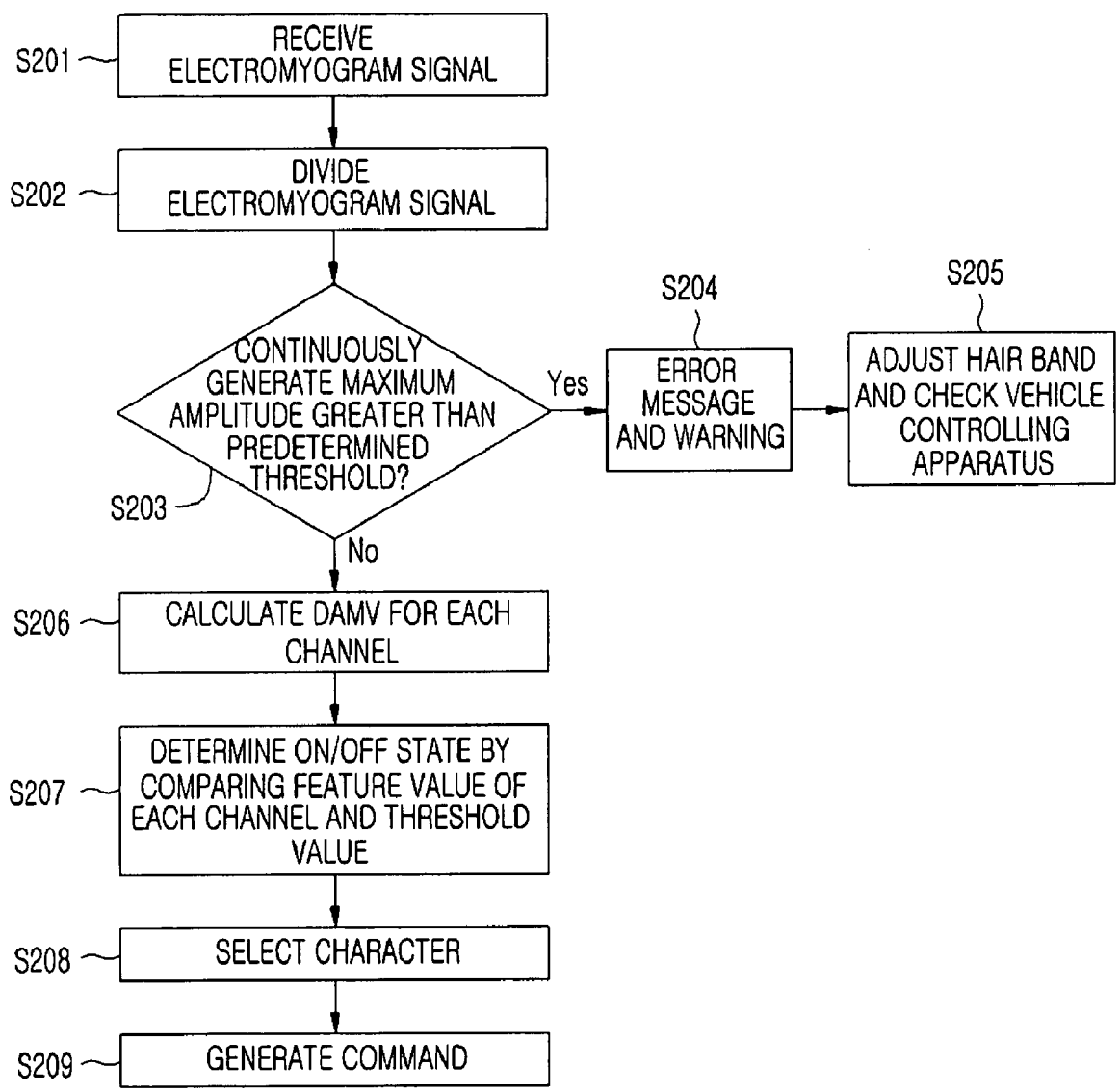
FIG. 3 is a flowchart of a method for selecting and outputting a character by teeth clenching according to an embodiment of the present invention.

FIG. 3 is a flowchart of a method for selecting and outputting a character by teeth clenching according to an embodiment of the present invention.

Referring to FIG. 3, the electromyogram sensors 100 senses the electromyogram signal generated from the temporalis muscle when a user makes a teeth clenching motion. Then, the amplifying and transmitting unit 120 amplifies the sensed electromyogram signal, transforms the amplified signal to a digital signal and transmits the digital signal through a wireless link. The signal processing unit 20 identifies a teeth clenching pattern from the electromyogram signal transmitted from the signal obtaining and transmitting unit 10 and outputs characters according to the identified teeth clenching pattern. Such a method of selecting and outputting characters in the signal processing unit 20 will be described in detail, hereinafter.

The signal processing unit 20 receives the electromyogram signal transmitted from the signal obtaining and transmitting unit at step S201. Herein, it is preferable to use a Bluetooth protocol for the communication between the signal obtaining and transmitting unit 10 and the signal processing unit 20 because the Bluetooth protocol is suitable to a short range communication and consumes less power.

The received signal is processed through a preprocessing step at first. In the preprocessing step, the electromyogram signals inputted from two channels, i.e., a left channel and a right channel, are divided by a time block, i.e., 100 ms, at step S202 because electromyogram signals longer than 100 ms can be assumed as stationary. However, the length of the divided electromyogram signal may vary according to its condition. While transforming the electromyogram signal to a digital signal, about 1 kHz of sampling frequency is used. Therefore, 100 samples are obtained from each of the divided electromyogram signals.

The preprocessing step includes a step for detecting poor contacts of the electromyogram sensor 100 or the ground electrode 110 and generating the character creating command based on the detected poor contacts. The poor contacts maximize the amplitude of the electromyogram signal as a square wave. Accordingly, the signal processing unit 20 observes the electromyogram signals whether the maximum amplitudes greater than a predetermined threshold value are continuously generated or not at step S203. If the maximum amplitudes are continuously generated, the character constituting apparatus according to the present invention notices the error of detecting the electromyogram signal to the user by creating an error message or reproducing a predetermined sound at step S204. Then, the user adjusts the hair-band, or the character constituting apparatus is checked at step S205.

After the preprocessing step, features are extracted from the electromyogram signals at step S206. That is, a difference of absolute mean values is extracted from electromyogram signals obtained from two channels based on following equation.

$$DAMV = \frac{1}{N-1}\sum_{i=2}^{N}|x(i)-x(i-1)|$$

Herein, N denotes the number of samples in each of the divided electromyogram signals and x(i) represents the digital electromyogram signal value at an index i. Since the DAMV represents the characteristics of electromyogram signal which is rapidly changed and does not include direct current (DC) components, it does not require a step for eliminating the DC components.

Using the DAMV value, a pattern classification is performed at step S207. In the pattern classification, the feature values of electromyogram signals from two channels are compared with a predetermined threshold value. If the feature value is greater than the predetermined threshold value, the electromyogram signal from corresponding channel is classified into an ON state. On the contrary, if the feature value is smaller than the predetermined threshold value, the electromyogram signal is classified into an OFF state. That is, the electromyogram signals obtained from two channels are classified into four different state signals such as 1) the electromyogram signals from a first and a second channel are OFF states; 2) the electromyogram signal obtained from a first channel arranged at a left temple is the ON state and the electromyogram signal obtained from a second channel arranged at a right temple is the OFF state; 3) the electromyogram signal obtained from the first channel is the OFF state and the electromyogram signal obtained from the second channel is the ON state; and 4) the electromyogram signals obtained from the first and the second channels are both ON states. Such classified patterns are defined as REST, LEFT, RIGHT and BOTH. As described above, four basic commands can be created based on electromyogram signals from two channels. Herein, each pattern per block is stored as first order arrangement according to a time.

After defining basic patterns, a character in a keyboard is selected based on the generated basic pattern at step S208, and a command is generated at step S209 to input the selected character. The four basic patterns are not sufficient to create about 20 to 30 characters for English or Korean. Therefore, it needs to generate commands to select a target key and to select one of characters assigned to one key in a specially designed keyboard, for example, a keypad of a mobile communication terminal, such as a left shift command, a right shift command, a forward command, a backward command and a button activation command. Although those commands are generated, there is plenty of time required to select one of keys in a common keyboard for computer that has 108 keys. Therefore, a general numeral keypad for a telephone is used in the present embodiment, which is a 4×3 matrix type numeral keypad arrangement.

FIGS. 4A through 4C show keypads having a 4×3 matrix type arrangement.

FIG. 4A shows a keypad having a 4×3 matrix type arrangement which is widely used. Such a keypad arrangement includes a key having four characters P, Q, R and S. In the present embodiment, a keyboard having a 4×3 matrix type arrangement each having maximally three characters. FIGS. 4B and 4C show a keyboard having a 4×3 matrix type arrangement each having three characters for English and Korean. Numbers are generally arranged in the 4×3 matrix type keyboard as shown in FIGS. 4A to 4C. A name of each key is defined as K0~K9, K* and K#.

Meanwhile, a selection of key on such a keyboard is controlled by clenching left teeth or right teeth. Also, following four operations are defined according to the duration time for clenching the left side teeth and the right side teeth.

1. CLS: clenching left teeth shortly
2. CRS: clenching right teeth shortly
3. CLL: clenching left teeth long 4. CRL: clenching right teeth long Also, there are three both teeth clenching patterns to select one of three characters in the selected key.

5. CBS: clenching both teeth shortly
6. CBT: clenching both teeth shortly twice
7. CBL: clenching both teeth long As described above, total seven operations can be made to select a key and a character and to input the selected character. The described operations are only an example and there may be various ways of designing the operations according to the teeth clenching motions.

Figure 5:
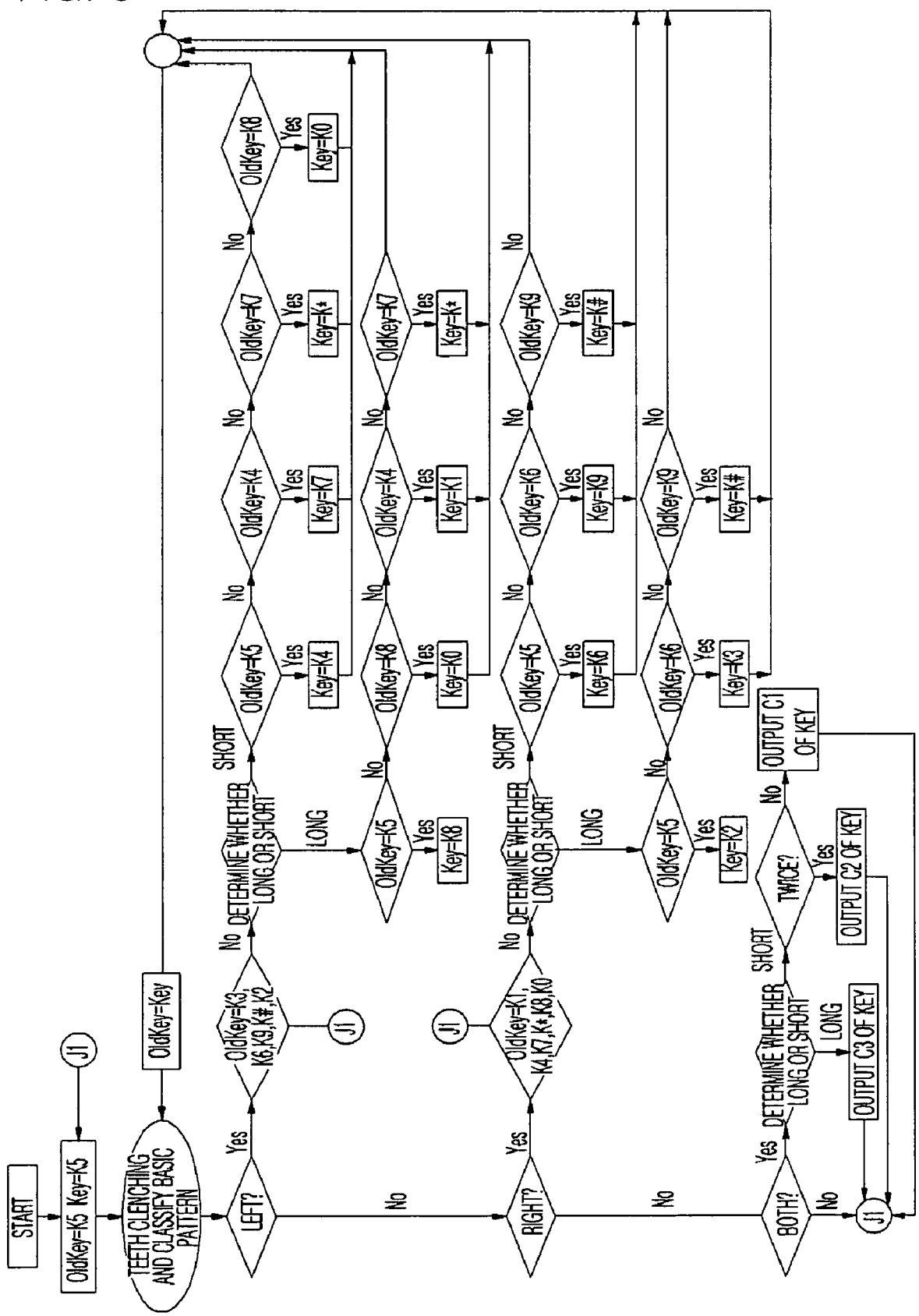
FIG. 5 is a flowchart showing a method of selecting and outputting a character by teeth clenching according to an embodiment of the present invention.

FIG. 5 is a flowchart showing a method of selecting and outputting a character by teeth clenching according to an embodiment of the present invention.

Referring to FIG. 5, values of past keys and a value of current key are initialized when a program or a system are started. Then, the electromyogram signal is obtained when a user makes a teeth clenching motion, and the obtained electromyogram signal is divided by a predetermined time. Then, basic patterns of teeth clenching are classified into, for examples, rest, left, right and both. If the teeth clenching motion made by a user is the left teeth clenching motion or the right teeth clenching motion, one of 12 keys is selected according to the duration of making corresponding teeth clenching motion as shown in the flowchart of FIG. 5. After a target key is selected, one of three characters in the selected key is selected according to the basic pattern of teeth clenching motion. The first, the second and the third character of each key are defined as C1, C2 and C3. After completely inputting the character, it returns to the initial stage. A method of selecting a key and a method of inputting a character will be described, hereinafter.

\* A Method of Selecting a Key

Figures 6, 7:
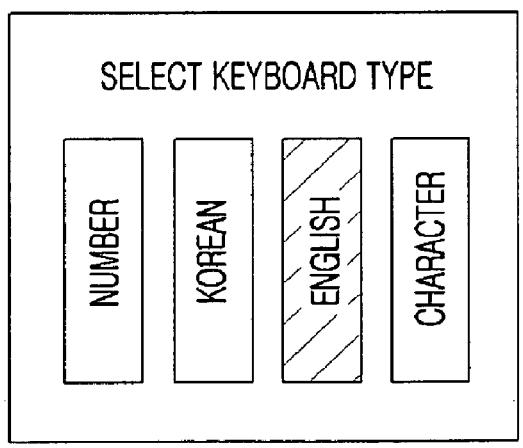
FIG. 6 is a diagram showing a method of selecting a key according to an embodiment of the present invention.
FIG. 7 is a view showing a keyboard type selection menu according to an embodiment of the present invention.

FIG. 6 is a diagram showing a method of selecting a key according to an embodiment of the present invention.

Referring to FIG. 6, when the apparatus for selecting and outputting a character according to the present invention is started, a key K5 is initially selected. In the present embodiment, keys are selected by clenching one side teeth shortly or long instead of alternatively clenching right teeth and left teeth because it is simpler and easier to a user. For example of 4 rows and 3 columns matrix type keyboard, left teeth is shortly clenched (CLS) to move an activation of key selection to a first column. In order to move the activation of key selection to an upper row, the left side teeth is clenched long (CLL). In order to move to a lower row, the left side teeth are shortly clenched (CLS). The left side teeth are shortly clenched again to move to a next lower row. In order to move to the third column, the right side teeth are shortly clenched (CRS). At this position, the right side teeth are clenched long (CRL) to move to the upper low. The right side teeth are shortly clenched (CRS) to move to the lower row. In the second column, a character at upper low is selected by clenching the right side teeth long (CRL), or a character at lower low is selected by clenching the left side teeth long (CLL). The keyboard having 12 keys is controlled as described above.

\* A Method of Canceling a Selected Key

If a user wants to cancel the key selection, a user must make following teeth clenching motions. The right side teeth are clenched (CRS or CRL) at the first column, or the left side teeth are clenched (CLS or CLL) at the third column. When the key K8 or K0 is selected, the right teeth are clenched (CRS or CRL). After the selected key is cancelled, the K5 is selected as an initial key.

\* A Method of Selecting One of Characters Assigned to a Selected Key

After selecting a key, one of three characters assigned to the selected key is selected. In case of an English keyboard shown in FIG. 4B, three characters E, W, and Q are assigned into the key K1. In order to select a character E, the both teeth are clenched shortly. The both teeth are clenched twice to select a character W, and the both teeth are clenched long to select the character Q.

\* A Method of Changing a Keyboard Type

In order to change the keyboard type from the English alphabet to the Korean alphabet or from the Korean alphabet to the English alphabet, the left teeth are clenched much longer than CLL. Then, a list of keyboard types is displayed, and one of keyboard types is selected by the left teeth clenching or the right teeth clenching. In order to confirm the selection, the both teeth are clenched. After then, the selected keyboard is displayed. Such a menu is shown in FIG. 7.

As described above, the apparatus and method for selecting and outputting character by clenching teeth according to the present invention allows a disabled person to conveniently communicate through inputting characters into information terminals such as a mobile phone or a notebook computer by sensing the electromyogram signals generated from the temporalis muscle of the disabled person and embodying as a form of wearable headgear such as a hair-band or a hat.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. An apparatus for selecting and outputting characters by a teeth clenching motion made by a user, comprising:

an electromyogram signal obtaining unit including electromyogram sensors disposed at both sides for generating an electromyogram signal according to a predetermined muscle activated when a user clenches teeth, and a ground electrode connected to a body of the user for providing a reference voltage; and an electromyogram signal processing unit for outputting a character by identifying a teeth clenching motion pattern of each block of teeth according to a side of teeth clenched, a duration of clenching teeth and consecutive clenching motions through analyzing the obtained electromyogram and selecting characters according to the identified teeth clenching motion pattern, wherein the electromyogram signal obtaining unit comprises:

a basic pattern identifying unit for dividing the electromyogram signal by a predetermined time, extracting characteristics from the divided electromyogram time blocks, comparing the extracted feature value with a predetermined threshold value, classifying the divided electromyogram time block into an On-state if the extracted feature value are larger than the threshold, classifying the divided electromyogram time block into an Off-state if the extracted feature value is smaller than the threshold, and identifying a basic teeth clenching motion pattern having one of values 'rest', 'left', 'right' and 'both';

a command generating unit for selecting a key location allocated on a keyboard through identifying a motion of clenching left teeth shortly, a motion of clenching right teeth shortly, a motion of clenching left teeth long and a motion of clenching right teeth long from a basic teeth clenching pattern of each block, and selecting one of characters in the selected key by clenching both side teeth shortly, clenching both side teeth twice and clenching both side teeth long; and a character displaying unit for displaying the keyboard, and outputting characters outputted from the command generating unit in video and audio, and wherein the dividing the electromyogram signal by a predetermined time is configure to obtain a difference of absolute means value (DAMV) as feature value from the divided electromyogram signals obtained from two channels by $DAMV = \frac{1}{N-1} \sum_{i=2}^{N} |x(i) - x(i-1)|$, where N denotes the number of samples in each of the divided electromyogram signals and x(i) represents the digital electromyogram signal value at an index i.

2. The apparatus of claim 1, wherein the command generating unit and the character displaying unit are included in separate equipments, and a wireless transmitting/receiving unit or an interface is further included to provide a wireless communication between the command generating unit and the character displaying unit.

3. The apparatus of claim 1, wherein the electromyogram signal obtaining unit further includes an amplifying/transmitting unit for amplifying the sensed electromyogram signal and transforming the amplified electromyogram signal to a digital signal, and the electromyogram signal processing unit further includes a receiving/amplifying unit for receiving the electromyogram signal from the electromyogram signal obtaining unit and amplifying the received signal.

4. The apparatus of claim 1, wherein the electromyogram signal obtaining unit is disposed at a fixing means including a hair-band and a hat.

5. The apparatus of claim 1, wherein the electromyogram sensors are provided in plurality.

6. The apparatus of claim 5, wherein the electromyogram sensors are a right sensor and a left sensor, which are arranged about both temples according to teeth clenching, and the ground electrode is arranged at a center of a forehead for measuring a reference voltage.

7. A method of selecting and outputting characters by a teeth clenching motion, comprising the steps of:

a) sensing an electromyogram signal of a predetermined muscle activated by a teeth clenching motion made by a user through electromyogram sensors;

b) dividing the sensed electromyogram signal by a predetermined time, extracting characteristics from the divided electromyogram time blocks, comparing the extracted characteristic value with a predetermined threshold, classifying the divided electromyogram time block into an On-state if the extracted characteristic value are larger than the threshold, classifying the divided electromyogram time block into an Off-state if the extracted characteristic value is smaller than the threshold, identifying a basic teeth clenching motion pattern having one of values 'rest', 'left', 'right' and 'both' at a basic pattern identifying unit, selecting a key location allocated on a keyboard based on the identified basic teeth clenching pattern of each block, and selecting one of characters in the selected key through a teeth clenching motion to completely input a corresponding character at a command generating unit; and c) outputting the selected character on a character displaying unit, wherein the step b) further comprises:

dividing the electromyogram signal by a predetermined time; obtaining a difference of absolute means value (DAMV) as feature value from the divided electromyogram signals obtained from two channels by $DAMV = \frac{1}{N-1} \sum_{i=2}^{N} |x(i) - x(i-1)|$, where N denotes the number of samples in each of the divided electromyogram signals and x(i) represents the digital electromyogram signal value at an index i.;

classifying the electromyogram signals into four basic patterns by comparing the obtained feature values of the electromyogram signals with a predetermined threshold value, classifying the electromyogram signals into an ON state if the feature value is greater than the predetermined threshold value and classifying the electromyogram signals into an OFF state if the feature value is smaller than the predetermined threshold value; and selecting a key location allocated on a keyboard through identifying a motion of clenching left teeth shortly, a motion of clenching right teeth shortly, a motion of clenching left teeth long and a motion of clenching right teeth long from the basic teeth clenching pattern of each block at a command generating unit, and selecting one of characters in the selected key by clenching both side teeth shortly, clenching both side teeth twice and clenching both side teeth long.

8. The method of claim 7, wherein the keyboard is configured of 12 keys in a 4.times.3 matrix type arrangement.

9. The method of claim 8, wherein a target key is selected by moving a key selection to a direction corresponding to a left teeth clenching motion or a right teeth clenching motion based on a center key set at the keyboard and the selected key is cancelled by making the right teeth clenching at the left or making the left teeth clenching at the right.

10. The method of claim 9, wherein one of characters included in the selected key is selected by clenching both teeth shortly, clenching both sides teeth twice or clenching both sides teeth long.

11. The method of any one of claims 9 and 10, wherein the center key is selected when the selected key is cancelled.

12. The method of claim 7, wherein a menu for selecting one of numbers, English alphabets, and Korean alphabets is displayed by making a left teeth clenching motion or a right teeth clenching motion for very long, a cursor indicating displayed options in menu is moved by making one of the left teeth clenching motion and the right teeth clenching motion, and the selected type of keyboard is displayed by clenching the both sides of teeth.

* * * * *